United States Patent [19]

Chaintron

[11] Patent Number: 4,934,095
[45] Date of Patent: Jun. 19, 1990

[54] METHOD FOR PROPAGATING AND GROWING PLANTS OF THE BROMELIACEAE FAMILY, AND PLANTS OBTAINED IN THIS WAY

[75] Inventor: Jean-Marc Chaintron, Orgerus, France

[73] Assignee: Societe de Creation et D'Obtention Vegetale et de Recherche Biotechnologique "Socotra", Garancieres, France

[21] Appl. No.: 238,498

[22] Filed: Aug. 31, 1988

[30] Foreign Application Priority Data

Aug. 31, 1987 [FR] France .................... 87 12100

[51] Int. Cl.$^5$ ............................... A01G 1/00
[52] U.S. Cl. ............................ 47/58; 47/DIG. 3
[58] Field of Search ............... 47/58, DIG. 3, 1.1

[56] References Cited

U.S. PATENT DOCUMENTS 4,253,274 3/1981 Gold .................... 47/DIG. 3
4,550,528 11/1985 Mehra-Palta et al. ...... 47/DIG. 3
4,793,095 12/1988 Stow .................... 47/DIG. 3

FOREIGN PATENT DOCUMENTS

WO 86/03934 7/1986 World Int. Prop. O.

Primary Examiner—David A. Scherbel
Assistant Examiner—Michele A. Van Patten
Attorney, Agent, or Firm—Dennison, Meserole, Pollack & Scheiner

[57] ABSTRACT

In a method of propagating and growing plants of the bromeliaceae family, in particular of the genus pineapple, to obtain ornamental pot plants, the plant is caused to grow in the usual way until a floral stalk carrying a fruit is formed and this floral stalk is cut and rooted in a pot filled with soil.

18 Claims, 1 Drawing Sheet

METHOD FOR PROPAGATING AND GROWING PLANTS OF THE BROMELIACEAE FAMILY, AND PLANTS OBTAINED IN THIS WAY

BACKGROUND OF THE INVENTION

1. Field of the Invention

The invention concerns a method for propagating and growing plants of the bromeliaceae family, especially of the genus pineapple, and plants obtained in this way.

2. Description of the Prior Art

Plants of this family comprise numerous genuses, subdivided into multiple varieties, which are cultivated for their fruit and/or their flowers, for consumption and/or decoration.

Plants of the genus pineapple are cultivated principally for their fruit for consumption, but some varieties, the fruits of which are of little interest from the consumption point of view, are cultivated as ornamental plants or to provide cut flowers to be kept in vases filled with water.

Plants of the bromeliaceae family, and those of the genus pineapple in particular, have a common characteristic in a stem that is provided with roots at its base and which features closely spaced nodes from which the leaves grow. During growth of the plant there grows from the stem and above the leaves a floral stalk also called the "inflorescence stem".

This floral stalk has different morphological characteristics to the stem and in particular has nodes that are much more widely spaced than those of the stem which it surmounts or extends.

As it grows, this floral stalk produces a flower or, to be more precise, a group of flowers the combined carpels of which have the characteristic appearance of the fruit which will develop from the flowers.

The fruit which develops from the flowers is generally surmounted by a ring or "tuft" of leaves, the leaves in which are identical to those which form at the base of the plant, but shorter.

As it grows the plant produces buds which grow from the stem in particular and some of which form shoots.

For propagation selected shoots are separated from the parent plant as cuttings to produce other plants which in turn produce a fruit.

When a plant of the genus pineapple is cultivated for consumption, the fruit is gathered by cutting the floral stalk just below the fruit, when the latter has reached maturity or a stage close to maturity.

When a plant of the genus pineapple is cultivated for ornamental purposes, either the potted plant or the cut flower, that is to say the floral stalk surmounted by the flower and/or the fruit, is marketted.

The potted plant has the main disadvantage of being particularly bulky and difficult to transport since its average diameter is generally in the order of 50 to 70 cm.

As for the cut flower, its main disadvantage is that is has a relatively short life in water, three weeks to one month maximum, and it is difficult to display in a vase, given the relatively great weight of the fruit which surmounts the floral stalk.

An object of the invention is to remedy the above-mentioned disadvantages by providing a method of propagating and growing plants of the bromeliaceae family whereby ornamental plants of a new kind may be obtained.

It has been found, surprisingly, that plants of this family can be propagated from a part of the plant which until now has never been used or proposed for use for the purposes of reproduction or propagation.

In the prior art the plant is principally reproduced, as already explained, by cuttings consisting of shoots selected according to precise criteria.

More or less successful attempts have been made to reproduce these plants from the other parts of the plant, for example the stem or leaves.

It has now been found that it is possible to propagate the plant from the floral stalk, under well defined conditions.

SUMMARY OF THE INVENTION

In one aspect, the invention consists in a method of propagating and growing plants of the bromeliaceae family, in particular of the genus pineapple, to obtain ornamental pot plants, in which method of plant is caused to grow in the usual way until a floral stalk carrying a fruit is formed and this floral stalk is cut and caused to root in a pot filled with soil.

The invention provides for the floral stalk to be cut at a stage in its development where it carries a fruit in the process of formation.

There is obtained in this way an ornamental pot plant differing from known pot plants since it consists of a floral stalk surmounted by a fruit.

Unlike known pot plants, it has no stem, no bulky leaves and is easier to transport, the few exterior leaflets being no trouble.

While this pot plant resembles the traditional cut flower, it is nevertheless a rooted plant with a much longer life than the cut flower.

Where circumstances are favorable, leaves may appear after several months, for example, in place of the fruit which will in the meantime have dried out.

This method of propagating and growing applies to all plants of the bromeliaceae family, in particular to those of the genus pineapple, but also to those of the genus Vriesia, Guzmania, etc.

According to another characteristic of the invention, the floral stalk is cut at a stage of development where the flower, which has produced the fruit, has fallen off and there remain only the carpels of the flower which together constitute the fruit in the process of formation. The floral stalk is usually cut between the 15th and the 60th day after floral induction.

This cutting may therefore be done at a later or earlier stage in the maturing of the fruit, given that it is generally preferable to do it at an early stage in the formation of the fruit.

According to another characteristic of the invention, the floral stalk is cut at any point below the fruit and above the junction between the floral stalk and the stem. It is therefore possible to obtain a floral stalk of the required length, according to the esthetic and dimensional characteristics required of the ornamental plant.

The cutting is preferably done between two successive nodes of the floral stalk or, as an alternative to this, slightly below the junction between the floral stalk and the stem.

To facilitate rooting of the floral stalk in its nutrient medium, that is to say in the soil in the pot, natural or synthetic vegetable hormones are used.

Any of the hormones known for this purpose may be used, in particular those of the auxin and cytokinin type. These include: indolacetic acid, indolbutyric acid, napthenacetic acid, benzyladenine, benzylaminopurine and mixtures thereof.

In another aspect, the invention consists in an ornamental pot plant obtained through the previously defined propagation and growth method.

These ornamental plants have specific morphological characteristics which distinguish them from previously known ornamental plants of the bromeliaceae family.

The following description, given by way of example only, refers to the appended drawings.

DESCRIPTION

Figure 1:
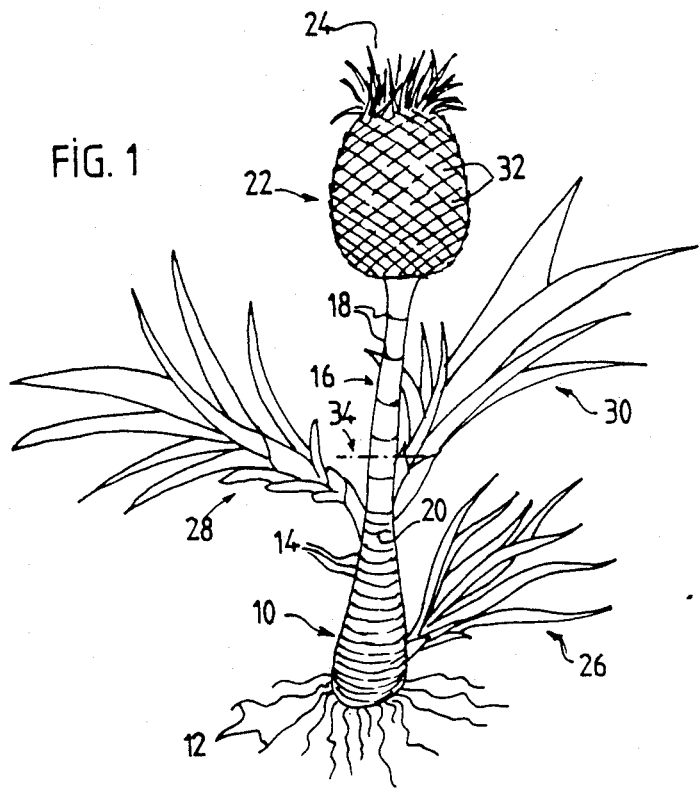
FIG. 1 is a simplified representation of a plant of the genus pineapple carrying a developing fruit.

The plant shown in FIG. 1 has a stem 10 which has roots 12 at its base and nodes 14. From these nodes grow leaves that are not shown in FIG. 1 in order to simplify it. Above the stem 10, and extending the latter, the plant has a floral stalk 16 the nodes 18 of which are much further apart than the nodes 14 of the stem 10. The floral stalk 16 joins the stem 10 approximately at the level of a tendril 20. At its top the floral stalk 16 bears a fruit 22, in this instance a pineapple which is surmounted by a ring or tuft of leaves 24.

The plant also has a number of shoots such as those shown at 26, 28 and 30 which are formed from buds that appear on the stem of the plant. As already explained, selected shoots are separated from the parent plant to produce other plants.

To implement the inventive method, the plant is caused to grow until the floral stalk 16 forms and this floral stalk is cut at a stage in development where the flower, which produced the fruit, has fallen off and there remain only the carpels 32 of the flower which together constitute the fruit in the process of formation and which have a characteristic scale-like appearance. The floral stalk is usually cut between the 15th and 60th day after floral induction.

When the plant has reached this stage of development, the floral stalk 16 is cut at a location selected to produce a floral stalk of the required length. This cutting is done at any place below the fruit 22 and above the junction 20 between the floral stalk and the stem, preferably between two consecutive nodes 18. In the specific case of FIG. 1 this cutting is done as shown by the chain-dotted line 34.

After cutting and to favor rooting of the floral stalk in a pot natural or synthetic vegetable hormones are used, preferably of the auxin or cytokinin type. The following may be used, for example: indolacetic acid, indolbutyric acid, naphthenacetic acid, benzyladenine, benzylaminopurine and mixtures thereof.

The treatment is applied by dipping the base of the cut floral stalk into a solution of these vegetable hormones and/or by impregnating the growth medium, that is to say the soil in the pot, with this same solution.

Figure 2:
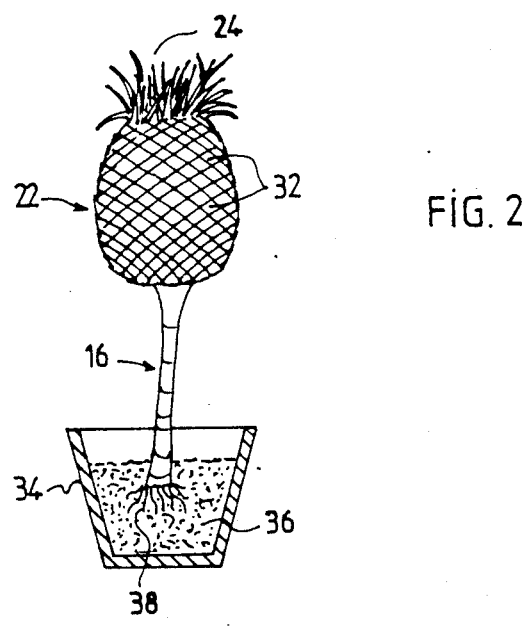
FIG. 2 is a simplified representation in partial cross-section of an ornamental pot plant in accordance with the invention, obtained by cutting and potting the floral stalk of the plant shown in FIG. 1.

FIG. 2 shows the ornamental plant obtained after rooting of the floral stalk 16 in a pot 34 filled with an appropriate medium 36. Because of the use of the aforementioned vegetable hormones, roots 38 develop at the base of the previously cut floral stalk and there is obtained in this way a new type of ornamental pot plant consisting essentially of the floral stalk 16 surmounted by the fruit 22. This ornamental plant has a much longer life than the cut flower obtained until now by cutting the floral stalk and keeping it in a vase filled with water. The fruit of the inventive ornamental plant can have a life of several months, especially if the floral stalk is cut at an early stage in the development of the fruit.

If circumstances are favorable, the ornamental plant may after several weeks or a few months produce leaves which replace the fruit which will in the meantime have dried out and been cut off.

There is claimed:

1. Method of propagating and growing a plant of the bromeliaceae family to obtain an ornamental pot plant, comprising:
    (a) causing said plant to grow until a floral stalk having a fruit therein is formed from a stem of said plant;
    (b) cutting said floral stalk to obtain a portion of said floral stalk having a fruit thereon; and
    (c) causing said portion of said floral stalk having a fruit thereon to root in soil, 2. Method according to claim 1, wherein the floral stalk is cut at a stage of development in which it carries a fruit in the process of formation.

3. Method according to claim 1, wherein the floral stalk is cut at a stage in development at which the flower which produced the fruit has fallen off and there remain only the carpels of the flower which together constitute the fruit in the process of formation.

4. Method according to claim 1, wherein the floral stalk is cut at a point below the fruit and above the junction between the floral stalk and the stem, chosen to obtain a floral stalk of the required length.

5. Method according to claim 1, wherein the floral stalk comprises a plurality of nodes and is cut between two successive nodes.

6. Method according to claim 1, wherein the floral stalk is cut slightly below the junction between the floral stalk and the stem.

7. Method according to claim 1, wherein natural or synthetic vegetable hormones are added to the soil to promote the rooting of the floral stalk.

8. Method according to claim 7, wherein the hormones are of the auxin or cytokinin type.

9. Method according to claim 8, wherein the hormones are chosen from the group comprising indolacetic acid, indolbutyric acid, naphthenacetic acid, benzyladenine, benzylaminopurine and mixtures thereof.

10. Ornamental pot plant of the bromeliaceae family obtained by a method comprising:
    (a) causing a plant to grow until a floral stalk having a fruit thereon is formed from a stem of said plant;
    (b) cutting said floral stalk to obtain a portion of said floral stalk having a fruit thereon;
    (c) causing said portion of said floral stalk having a fruit thereon to root in a pot of soil, producing said ornamental pot plant.

11. Plant according to claim 10, wherein the floral stalk is cut at a stage of development in which it carries a fruit in the process of formation.

12. Plant according to claim 10, wherein the floral stalk is cut at a stage in development at which the flower which produced the fruit has fallen off and there remain only the carpels of the flower which together constitute the fruit in the process of formation.

13. Plant according to claim 10, wherein the floral stalk is cut at a point below the fruit and above the junction between the floral stalk and the stem, chosen to obtain a floral stalk of the required length.

14. Plant according to claim 10, wherein the floral stalk comprises a plurality of nodes and is cut between two successive nodes.

15. Plant according to claim 10, wherein the floral stalk is cut slightly below the junction between the floral stalk and the stem.

16. Plant according to claim 10, wherein natural or synthetic vegetable hormones are added to the soil to promote the rooting of the floral stalk.

17. Plant according to claim 16, wherein the hormones are of the auxin or cytokinin type.

18. Plant according to claim 17, wherein the hormones are chosen from the group comprising indolacetic acid, indolbutyric acid, naphthenacetic acid, benzyladenine, benzylaminopurine and mixtures thereof.

* * * * *